United States Patent
Robinson et al.

(10) Patent No.: US 6,581,069 B1
(45) Date of Patent: Jun. 17, 2003

(54) AUTOMATED ACTIVATION AND DEACTIVATION OF OPERATIONAL DATA LOGGING ON MEDICAL IMAGING DEVICE

(75) Inventors: Naja S. Robinson, Menomonee Falls, WI (US); Lawrence E. Ploetz, Brookfield, WI (US); Jie Xue, Waukesha, WI (US)

(73) Assignee: GE Medical Technology Services, Inc., Waukesha, WI (US)

( * ) Notice: Subject to any disclaimer, the term of this patent is extended or adjusted under 35 U.S.C. 154(b) by 329 days.

(21) Appl. No.: 09/585,218

(22) Filed: Jun. 1, 2000

(51) Int. Cl.[7] .............................................. G06F 17/30
(52) U.S. Cl. ................................................... 707/104.1
(58) Field of Search .................. 707/104.1; 166/254.2; 340/286.07, 825.36; 382/115, 131; 455/405; 600/410, 454; 705/213; 709/216; 702/183, 185; 714/10

(56) References Cited

U.S. PATENT DOCUMENTS 4,914,686 A * 4/1990 Hagar, III et al. .......... 455/405
5,442,541 A * 8/1995 Hube et al. ..................... 700/9
6,377,162 B1 * 4/2002 Delestienne et al. ... 340/286.07
6,381,557 B1 * 4/2002 Babula et al. ............... 702/183

* cited by examiner

Primary Examiner—Diane D. Mizrahi
Assistant Examiner—Apu M Mofiz
(74) Attorney, Agent, or Firm—Ostrager Chong & Flaherty LLP

(57) ABSTRACT

A method and a system for automatically activating and deactivating a data logging function on a remotely located medical imaging device from a central service facility in response to acquisition of updated service contract information. Customer profiling and service contract data are automatically processed at a central facility to detect that a medical imaging device is now under contract to receive regular scanner utilization reports. The scanner data logging function is then automatically turned on from the central facility. The central facility then monitors the receipt of scanner data log files to ensure that the first data log file has been successfully transmitted from activated medical imaging device, for processing and subsequent utilization report delivery. In the case of an expired service contract, the data logging feature on the medical imaging device is automatically deactivated from the central facility.

23 Claims, 10 Drawing Sheets

| FIG. 4A |
|---|
| FIG. 4B |

| FIG. 7A |
|---------|
| FIG. 7B |

AUTOMATED ACTIVATION AND DEACTIVATION OF OPERATIONAL DATA LOGGING ON MEDICAL IMAGING DEVICE

FIELD OF THE INVENTION

This invention relates generally to centralized generation of reports which compile and/or summarize operational data from remotely located user-operated electronic devices, for example, imaging devices used for medical diagnosis.

BACKGROUND OF THE INVENTION

Diagnostic imaging systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic imaging systems. These include computed tomography (CT) systems, x-ray systems (including both conventional and digital or digitized imaging systems), magnetic resonance (MR) systems, positron emission tomography (PET) systems, ultrasound systems, nuclear medicine systems, etc. In many instances, these modalities complement one another and offer the physician a range of techniques for imaging particular types of tissue, organs, physiological systems, etc. Health care institutions often arrange several such imaging systems at a single facility or at multiple facilities, permitting its physicians to draw upon such resources as required by particular patient needs.

Modern medical diagnostic imaging systems typically include circuitry for acquiring image data and for transforming the data into a useable form, which is then processed to create a reconstructed image of features of interest within the patient. The image data acquisition and processing circuitry is referred to as a "scanner" regardless of the modality if physical or electronic scanning occurs as part of the imaging process. The particular components of the system and related circuitry, of course, differ greatly between modalities due to their different physics and data processing requirements. The terms "scanner", "medical imaging device" and "diagnostic imaging device" will be used interchangeably herein.

Medical diagnostic systems of the type described above are often called upon to produce reliable and understandable images within demanding schedules and over a considerable useful life. To ensure proper operation, the systems are serviced regularly by highly trained personnel who address imaging problems, configure and calibrate the systems, and perform periodic system checks and software updates. Moreover, service offerings have been supplemented in recent years by service centers capable of contacting scanners at subscribing institutions directly without the need for intervention on the part of the institution personnel. Such centralized servicing is intended to maintain the diagnostic systems in good operational order without necessitating the attention of physicians or radiologists, and is often quite transparent to the institution.

In certain centralized servicing systems, a computerized service center will contact a scanner via a network to check system configurations and operational states, to collect data for report generation, and to perform other useful service functions. Such contacts can be made periodically, such as during system "sweeps", in which a variety of system performance data is collected and stored with historical data for the particular scanner. The data can then be used to evaluate system performance, propose or schedule visits by service personnel, and the like.

While such service techniques have proven extremely valuable in maintaining diagnostic systems, further improvements are still needed. Although the transparency of interactions between scanners and service centers avoids distracting medical personnel with service updates unnecessarily, some degree of interaction between service centers and institutions is highly desirable. In particular, an interactive service system facilitates valuable exchanges of information, including reports of system performance, feedback on particular incidents requiring attention, updates of system licenses, software, imaging protocols, etc. Currently available service systems permit such interactive exchanges. In particular, a platform has been developed that serves as a base for the interactive servicing needs of different modalities. This platform allows a central service center to exchange information on possible service problems with remotely located scanners, and to retrieve information or data log files from scanners for the purpose of servicing those scanners. One known platform provides a uniform interface permitting clinicians and radiologists to operate a variety of scanners in different modalities, and to report service issues for the scanners, via a uniform, intuitive format.

The known integrated user-interactive platform for servicing diagnostic equipment at remote locations may be configured in software, hardware, or firmware at the scanner or may be installed in a central operator's station linking several scanners in a medical facility. The user interface permits service requests to be generated prior to, during or subsequent to examinations executed on the diagnostic equipment. The user interface also permits service messaging, report generation and retrieval, etc. The user interface is preferably configured as a network browser, which also facilitates linking the scanner or the central facility control station to a network such as an intranet or internet. The same user interface may be integrated into scanners of different modalities, thereby further facilitating service requests and the like by operations personnel, without requiring the personnel to become reacquainted with diverse interfaces in a facility.

In particular, the existing user-interactive platform provides the system user with the capability to request scanner utilization reports from a central service center based on the operational history of scanners at a remote facility. In order to provide such utilization reports, it is necessary to regularly collect operational data from these scanners. In accordance with an existing system, a scanner can be programmed to collect its own operational data in computer memory and then proactively transmit that data to a central facility in accordance with a preprogrammed schedule input to the scanner by the central facility only scanners covered by a service contract which provides for data logging and report generation will transmit logged operational data to the central facility. After the central facility has collected and processed the log files of operational data from all scanners covered by contracts, scanner utilization reports can be generated. In particular, a hospital administrator can at any time request, via a wide-area network or the Internet, a utilization report compiling and/or summarizing collected operational data for medical imaging devices (i.e., scanners) under contract at that hospital.

In accordance with the foregoing pre-existing system, a data logging program is stored in each scanner, but is not activated until that scanner is covered by an appropriate service contract. Similarly, when a service contract covering a particular scanner expires, the data logging feature incorporated in that scanner needs to be deactivated. There are several disparate computational systems involved in the collection of operational data from scanners, i.e., the contract system, the connectivity system and the scanners themselves. It is currently a manual process to tie these systems together. In particular, a manual process is currently used to turn on or off the data logging feature on a scanner. In the case of new service contracts, sometimes utilization reporting service is not provided on time due to delays in manually activating scanners. In the case of expired service contracts, utilization reporting service is often provided for free for many months beyond the service contract termination date due to delays in manually deactivating scanners.

Thus there is a need for an operational model which can automatically activate the data logging functionality in a scanner when a new service contract is started, and which can also deactivate the data logging functionality once the service contract has expired. This operational model should also automatically activate and deactivate the associated report delivery process.

SUMMARY OF THE INVENTION

The invention is directed to a method and a system for automatically activating and deactivating an operational data logging functionality on a remotely located medical imaging device from a central service facility. In particular, the preferred embodiment is directed to a method comprising the steps of: automatically processing contract data at a central facility to detect that a medical imaging device is now under contract to receive regular scanner utilization reports; automatically and remotely turning on the scanner data logging feature from the central facility; and monitoring scanner data log files received at the central facility to ensure that the first data log file has been successfully transmitted from the activated medical imaging device, for processing and subsequent utilization report delivery. In the case of an expired service contract, the data logging feature on the medical imaging device is automatically deactivated from the central facility.

In accordance with a further aspect of the preferred embodiment, the associated report delivery function is also automatically activated and deactivated concurrently with activation and deactivation of the data logging function on scanners covered by the new or expiring service contract. The reports are delivered over a wide-area network, e.g. the Internet, in response to requests for access from customers. A report server for providing web-based utilization reports may be located far away from the central service facility where data log files are received.

In addition, in accordance with the preferred embodiment, corrective action is taken by the central facility in the event that automatic activation or automatic deactivation of the scanner data logging function fails. The central service facility further incorporates an Administration Tool for generating reports tracking the data logging service status of all scanners under contract.

Every time a customer enters into a service contract to receive scanner utilization reports based on logged data from scanners, customer information and contract specifications are entered into a service contract database, as with any other service feature provided by the central service facility.

In accordance with the preferred embodiment of the invention, this customer profiling and service contract information is automatically and periodically extracted from a central service contract database as a so-called Extraction Output File. The records in the Extraction Output File are compared by an operation server with records in a so-called Contract Table, maintained in a local database by the same operation server. Any differences are entered in the local database, i.e., new and changed records detected in the Extraction Output File are added to the Contract Table, while records found in the Contract Table but not found in the Extraction Output File are removed from the Contract Table. These differences indicate new contracts, expired contracts, changes in the terms of a contract, etc. New medical imaging devices that were not previously in the local database are tracked for contract start date. Existing medical imaging devices that are in the local database, but do not appear in the Extraction Output File, are tagged for turning off of the data logging functionality.

In accordance with the preferred embodiment of the invention, a list of actions are automatically sent from the operation server to an automated support center server for activating and deactivating scanners. In particular, the automated support center server sends a command to turn on (or off) the data logging functionality of a specific medical imaging device and schedule proactive transmission of the operational data back to the automated support center server via a proactive diagnostics process. If the activation attempt by the automated support center server fails, a system administrator is automatically notified so that manual intervention may occur. If the first scanner data log file is not received within a predetermined number of days (e.g., 2 days) of the assigned expected reception date, again the system administrator is automatically notified to intervene to ensure that the data logging feature is turned on and that connectivity between the remote scanner and the automated support center server has not been lost. Conversely, when a scanner is turned off, the system administrator is automatically notified if scanner operational data continues to arrive at the automated support center server after the assigned termination date.

DETAILED DESCRIPTION OF THE PREFERRED EMBODIMENTS

The present invention is directed to a system and a method for providing information to support the work, process, patient flow and clinical practice of a radiology department. Each scanner in the radiology department sends operational data to a central server for processing. The data collected will measure the key scanner parameters based on key department productivity, quality and patient satisfaction goals and objectives. Based on the data collected, scanner utilization reports are generated at a central location. These reports can be accessed by customers via the Internet. The scanners include computerized tomography (CT) systems, magnetic resonance (MR) systems, ultrasound imaging systems, or any other type of computerized medical imaging device.

Figure 1:
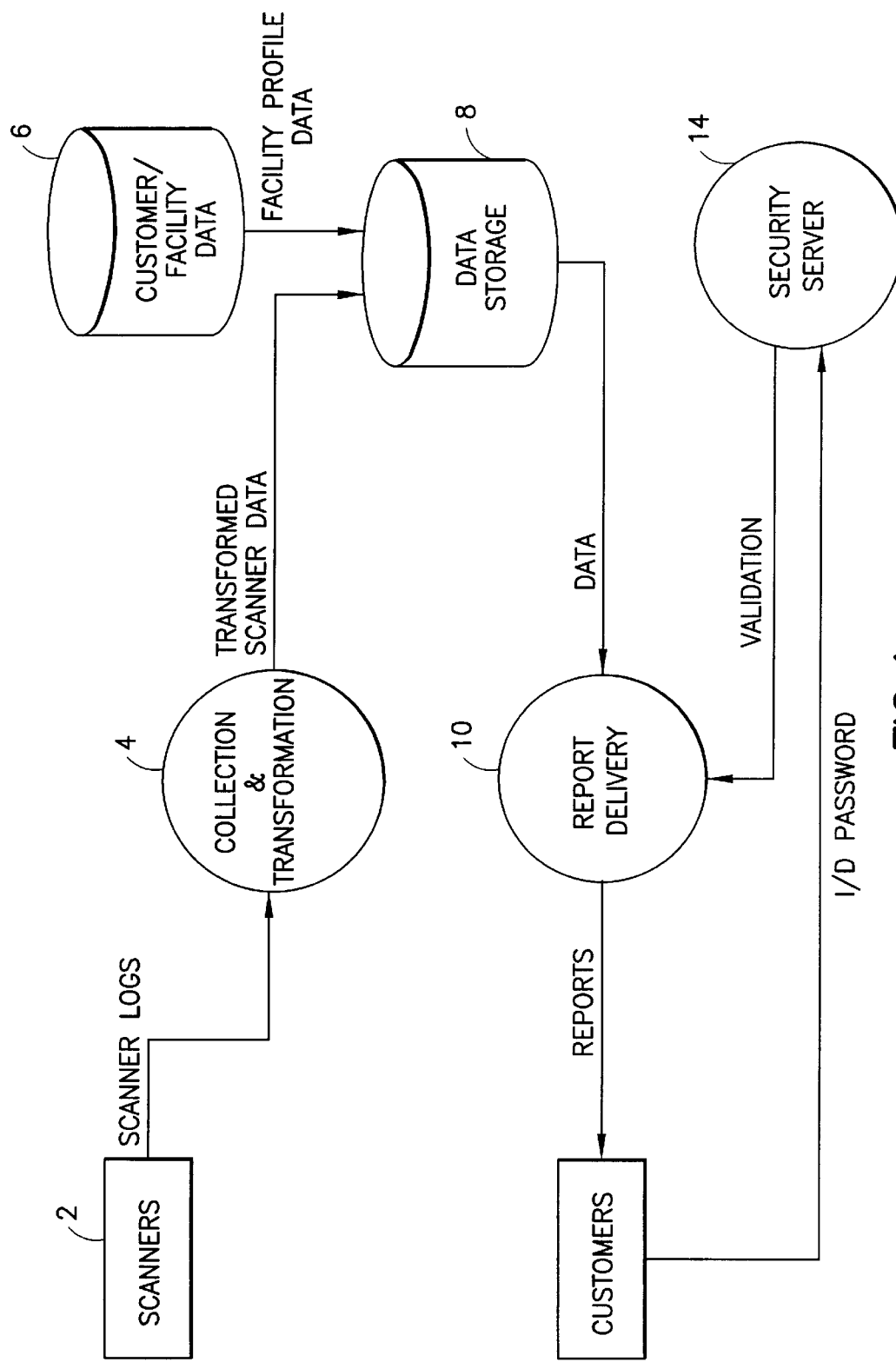
FIG. 1 is a diagram showing the flow and processing of operational data from remotely located scanners in accordance with the preferred embodiments of the present invention.

The high-level flow of data and processing is shown in FIG. 1. Each scanner 2 sends logs of operational data to a central processor 4 for collection and transformation. The transformed data is stored in data storage 8, along with medical facility profile data read from a customer/facility database 6. The stored data is periodically sent to a report delivery system 10. Customers 12 can access those reports provided they have inputted a valid and authentic security factors (e.g., ID and password) to a security server 14. The security server sends the validation to the report delivery system 10.

Figure 2:
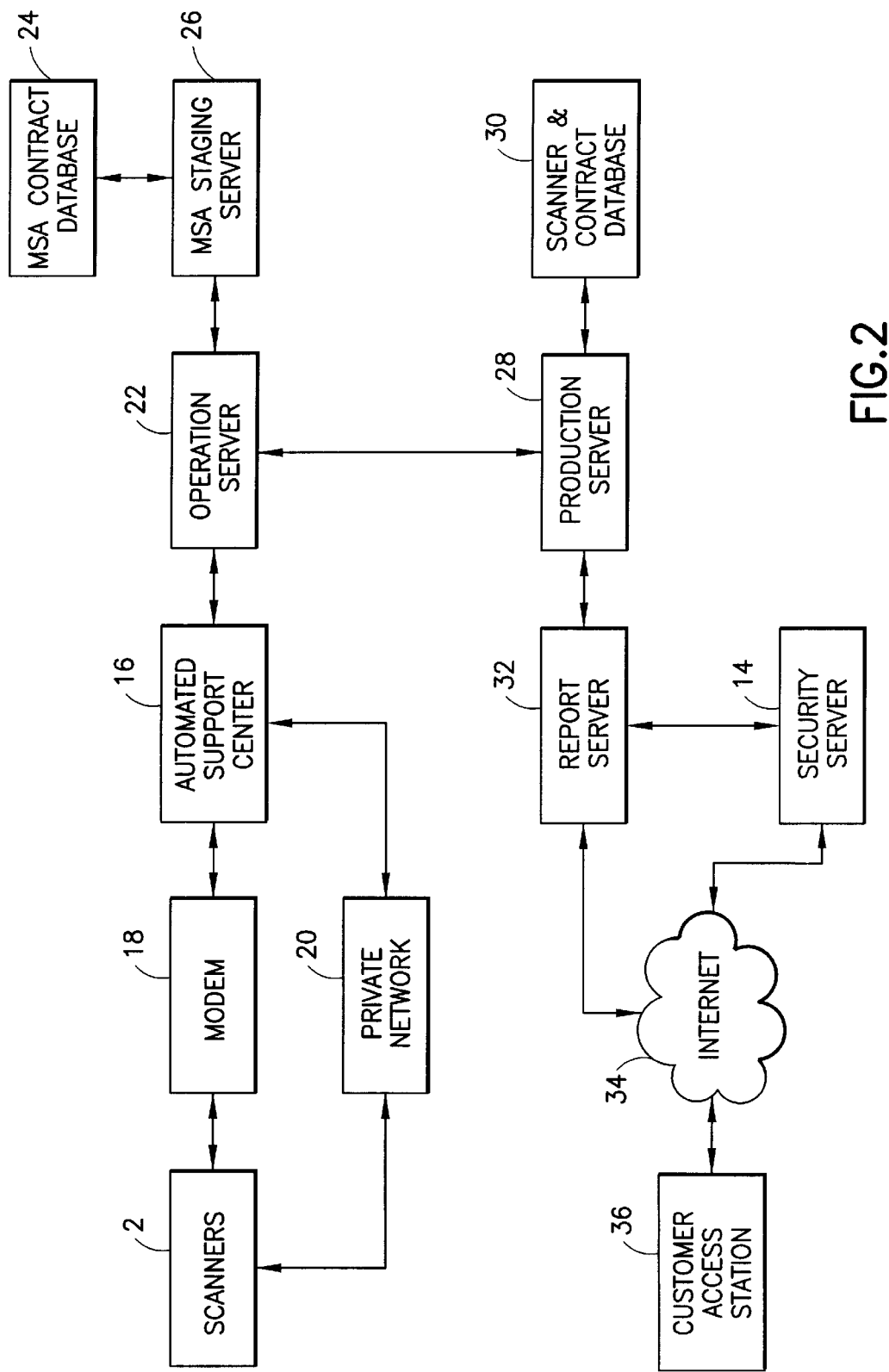
FIG. 2 is a block diagram showing the architectural component interaction of the system in accordance with the preferred embodiments of the invention.

Referring to FIG. 2, data is collected from each scanner 2 by an automated support center server 16 via a modem 18, a private network 20, or any other suitable communications channel. Each scanner is programmed to log specified operation-related data and then send that logged data to the automated support center server 16.

The preferred scanner output format comprises system data and exam data. The system data includes, but is not limited to, a time stamp indicated when a new exam began, the scanner modality, the product name, a system ID (i.e., a unique ID for a scanner for a particular customer at a particular location), a so-called Unique System Number (a unique key for a scanner, regardless of time, location and ownership), a so-called Mobile Location Number (used to track the particular location of the scanner at a particular time), and the hospital name. The exam data includes, but is not limited to, the same time stamp, the exam date, the start and end times for the exam, an exam number, a patient ID, patient age, patient sex, patient weight, patient history, patient status, a radiologist ID, a referring ID, an operator ID, an exam description, exam data, series and exam type in the form of a so-called current protocol terminology (CPT) code. The scanner transfers this data to the automated support center server 16 using a proactive diagnostics transfer mechanism. The scanner will use a data logging service ID when doing the proactive diagnostic data transfer mechanism. The scanner is programmed to transfer this data based on the time since the last transfer or when the data reaches a specified size threshold. The maximum time between transfers and the data size threshold are configurable per scanner. Also the time when the operational data is sent to the automated support center server is configurable per scanner.

The automated support center server 16 stores the scanner data files by USN, MLN or a combination of the two. The automated support center server 16 notifies an operation server 22 whenever a new file arrives, that was sent with the data logging service ID, by sending the file to the operation server via an internal network of the service provider. The automated support center server 16 logs an error message and notifies the appropriate system administrator if it cannot successfully send the data file to the operation server 22. The automated support center server 16 also provides a mechanism that allows the system administrator to remotely enable or disable the data logging feature and proactive diagnostics data transfer on a scanner system that is authorized to have its logged data reported pursuant to a valid service contract. When a scanner site is activated or deactivated, the automated support center server 16 notifies the operation server 22 with the new state of scanner site.

Every time a customer enters into a service contract to receive scanner utilization reports based on logged data from scanners covered by the contract, the customer profiling information and contract specifications are entered into a service contract database, as with any other service feature provided by the central service facility. In accordance with the preferred embodiment of the invention, this customer profiling and service contract information is automatically and periodically extracted from a central service contract database and compared by the operation server 22 to a table of customer profiling and contract information in a local database maintained by the operation server 22. Any differences between the records of the respective files are entered in the local database, i.e., new and changed records are added to the local database, while records corresponding to expired service contracts are removed from the local database. New scanners that were not previously recorded in the local database are tracked for contract start date. Existing scanners that are recorded in the local database, but which are covered by an expired service contract, are tagged for turn-off of their data logging functionality.

In accordance with the preferred embodiment of the invention, a list of actions are automatically sent from the operation server 22 to the automated support center server 16. The latter then sends a command to turn on (or off) the data logging functionality of a specific scanner 2 and schedule proactive transmission of the operational data back to the automated support center server via a proactive diagnostics process.

Once data logging begins, the operation server 22 validates the scanner files upon mail notification from the automated support center server 16 that a scanner data logging file has arrived. The validation comprises the following steps: identifying the file "grammar" (e.g., MR or CT); and verifying that all fields for the service product are present in the record and are of the correct type. If the record is not complete (i.e., missing field) or incorrect, it will be logged and deleted. The operation server 22 generates a CPT code based on scanner file data field values. The operation server 22 also encodes the required fields in a specified XML format. The operation server 22 send processed (i.e., transformed) scanner files in a compressed XML format to the production server 28 via the internal network of the service provider as soon as the files are processed.

The operation server 22 also records which scanner sites are sending data, the amount of data sent and the time the data was received. The operation server maintains an active site list/database, which is driven by contract information relating to maintenance service agreements (MSA). The MSA service contract information is received daily by the operation server from the MSA staging server 26 via the internal network of the service provider The server 26 in turn retrieves the contract information from an MSA contract information database 24. The operation server 22 notifies the system administrator if a scanner site in the active list has not sent a file in more than a configurable time period. Also, the operation server 22 serves a web page, intended for use in system administration, that displays a history of data reception frequency and data file size on a per scanner basis.

Still referring to FIG. 2, the data storage 30 receives XML-encoded scanner data from the production server 28 whenever the data is sent by the operation server 22. Derived data values such as the inter-exam time and exam duration are computed by the production server 28 and stored in the database 30. The data storage 30 also receives XML-encoded updated facility profile data from the production server 28 whenever that data is sent by the operation server 22.

In accordance with the preferred embodiment of the invention, the security server 14 is physically separate from the report server 32. The security server database is separate from the report server application database. Customer access to all reports is through a so-called Secure Socket Layer (SSL) on the Internet 34. The customer must upload a user ID and password or access code, via the Internet 34, to the security server 14. All user passwords and/or access codes are encrypted. The security server 14 validate users, determines their community membership, and assigns access privileges. Access privileges may be which reports are available to a customer based on that customer's service contract. The security server 14 allows validated users access to appropriate reports served from the report server 32 and transmitted to the customer's access station via the Internet 34.

All utilization reports generated by the report server 32 are based on the scanner data delivered to the production server 28. All graphical reports support a configurable display option that changes the appearance of the output (pie chart, bar chart, etc.). Preferably, the report server 32 delivers utilization reports which are compatible with Internet Explorer 4.01 or greater and Netscape 4.5 or greater on a Windows 95/98/NT platform. If the client is not compatible, then a message is sent to the user and a link to a compatible browser is displayed. The report server is also programmed to provide a configurable selection of time axes for reports. The report server generate reports that show trending and reports that show benchmarking.

Multiple report templates are supported. These may be grouped, each group including a number of reports. Access to groups may be based on user access. For example, the report server can generate and deliver reports that show study mix, study volume, image and series data by study type, volume by study mix, study mix by time of day and day of week, exam time by study mix, patient mix by exam duration, exam volume by time of day, system utilization by day of week, processing time for a CT scan by study mix, intra-exam time by study mix, exam duration, volume by radiologist, volume by referring physician, processing time for a CT scan by radiologist, exam time by technologist, patient volume (men and women) by age, study mix (number of exams) by referring physician, study mix (number of exams) by radiologist, and number of series and images per exam by radiologist.

The preferred embodiment of the invention is a web-delivered service product/capability that gives radiology departments critical decision support information for clinical practice (study, mix), operations management (volume, utilization), and customer demographics analysis (referring physician, patient age, etc.) centered on the "exam" step of patient service delivery.

The system in accordance with the preferred embodiment utilizes two types of data to generate the decision support reports, namely, scanner log data and facility profile data. The facility profile data are maintained for account tracking and data benchmarking purposes.

The data reporting process in accordance with the preferred embodiment is incorporated into a service contract management process. Facility profile data based on scanner utilization reporting service contracts is acquired and processed. A mechanism is established to automatically control, i.e., activate and deactivate, the data logging operation on scanners based on that service contract information. The operation server keeps track of the scanner status during daily production. A web-based user interface is used to administer the customer, contract and scanner status-related information.

Each service contract providing automatic data logging from a remote scanner to a central office and data reporting by the central office in response to customer requests transmitted over the Internet has at least the following information. (1) The name of the customer who signs the contract with service provider. A customer could be a multi-hospital corporate, a multi-site hospital facility or a single-site hospital facility. (2) The name of the hospital facilities covered under the contract. The facility may be the same as the customer for non multi-hospital corporate customers. (3) The detailed address of the hospital facility where the scanner is installed, including street address, city, state, country and postal code. (4) The system IDs of the scanners for each hospital facility covered under the contract. (5) For each scanner, an indicator showing which tier of a multi-tier service is under the contract. (6) The contract starting date for each scanner. (7) The contract ending date. It will be the same for all scanners. (8) User contact information.

Figure 3:
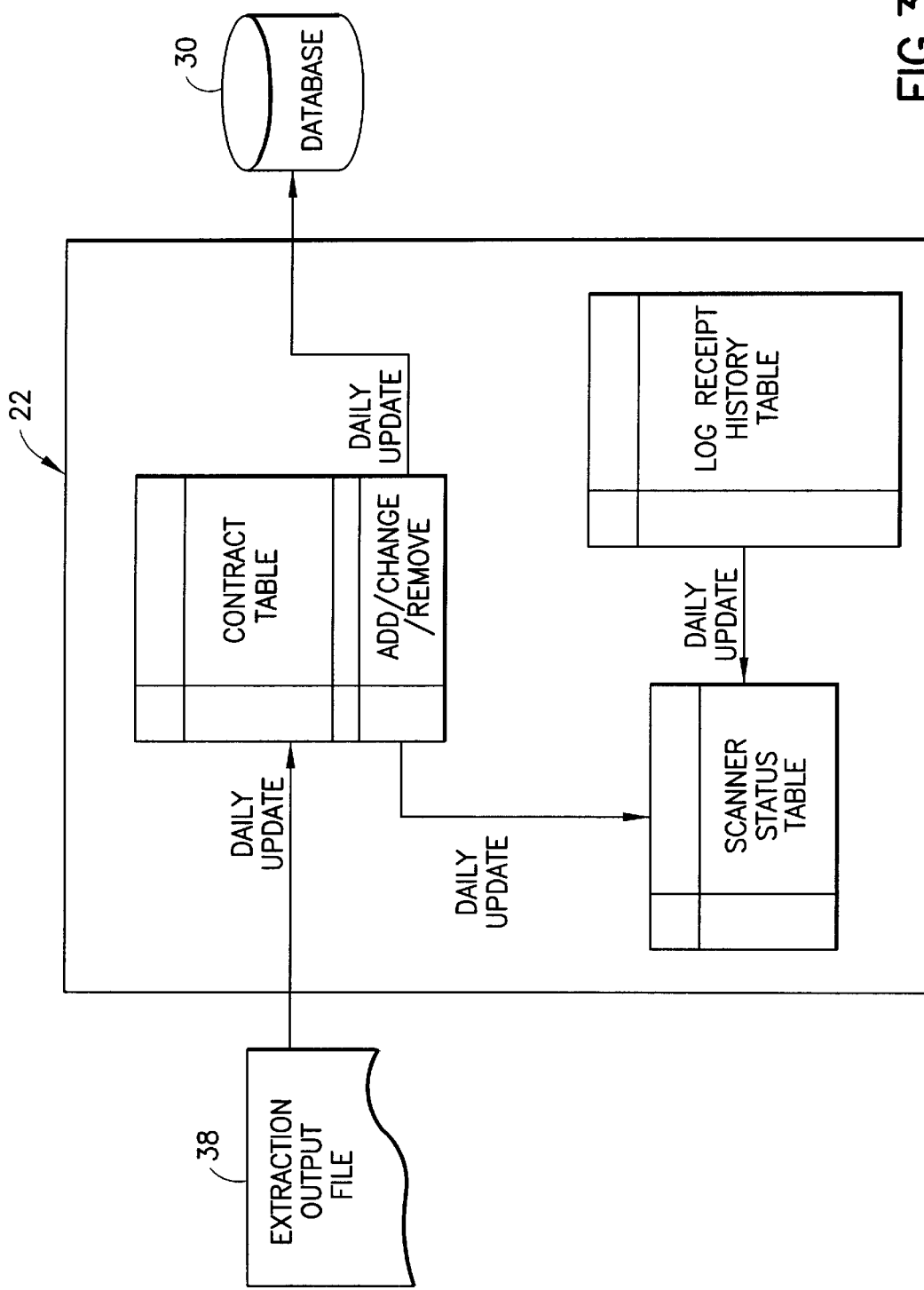
FIG. 3 is a diagram showing the flow of customer profiling, contract and scanner status data in accordance with the preferred embodiments of the invention.

FIG. 3 shows the data flow for customer profiling, contract and scanner status data. In accordance with the preferred embodiment of the invention, the operation server 22 (see FIG. 2) at the central service facility maintains a Contract Table and a Scanner Status Table. In addition, the operation server 22 incorporates a data preprocessor (not shown) which maintains a Log Receipt History Table. All three tables reside in an Oracle database. The Contract Table is updated daily in database 30.

The MSA staging server 26 (see FIG. 2) is programmed to extract customer profiling and contract data from pre-existing data sources, such as MSA contract database 24. Every scanner 2 that is covered by a valid scanner utilization reporting service contract will have a record(s) in the Extraction Output File 38 (see FIG. 3). One scanner may have multiple records reflecting multiple service contracts it has. The Extraction Output File has a header line including the date and time when the file was generated. Each record in the Extraction Output File has data fields as defined in Table 1 in the Appendix.

Preferably, the output file is a "|" delimited flat file of which one line represents one record. Preferably the file is generated daily. The Extraction Output File is stored on the MSA staging server 26 and is accessible by the operation server 22. The Extraction Output File may be overwritten during its daily refresh.

In accordance with the preferred embodiment shown in FIG. 2, the operation server 22 will fetch the MSA extraction file from the MSA staging server 26 in accordance with a schedule, e.g., daily at a certain hour. The operation server 22 is programmed to attempt to fetch the extraction file once an hour until successful. The operation server records an Alert in an Event Log if the file fetching fails a predetermined number of times, e.g., five times. The operation server renames the file to ScanPATH_YYYYMMDD.txt, with YYYY, MM, DD being the year, month and date of the receipt day, respectively.

In accordance with the preferred embodiment, the operation server maintains a database table, named Contract Table, to store all customer profiling and contract data extracted from the data sources. The Contract Table has one record for one scanner. Every scanner that is covered by a valid scanner utilization reporting service contract will have a record(s) in the Contract Table. Each record in the Contract Table will have the data fields as defined in Table 2 in the Appendix. The primary key of the Contract Table is a System ID/Contract Number/Rec-Key combination.

The operation server 22 also maintains a database table, named Contract Audit Table, to keep track of all the inserts/changes to the Contract Table. The contract audit table has fields for the :old and :new values of Table 2 fields 1 to 41, and also has a field for the Time/Date stamp when the audit record is inserted. To track inserts, an Insert Trigger is placed on the Contract Table so that the inserted record can be added to the :new value fields of the Contract Audit Table. To track changes, Change Triggers are placed on the Contract Table so that changed records can be added to the Contract Audit Table with the :old and :new values. The Contract Table fires the Change Trigger when any field marked as "Yes" in the "Change Audit?" column of Table 2 is changed, and the record has decision support features.

Figures 4, 4A:
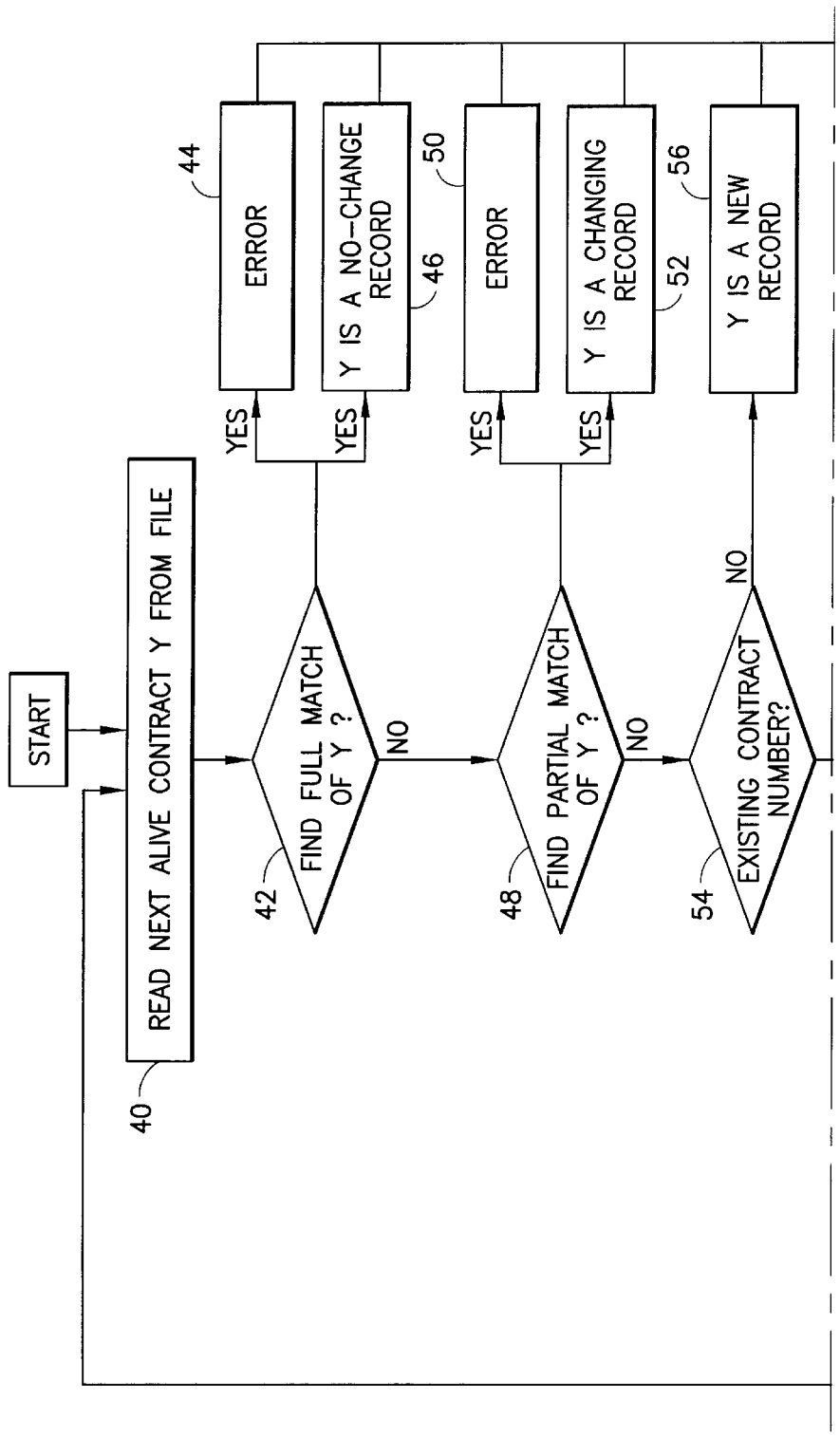
FIG. 4 is a flowchart showing the parsing operations performed by the operation server on the records of each Extraction Output File to generate a respective Contract Table in accordance with the preferred embodiments of the invention.
Figure 4B:
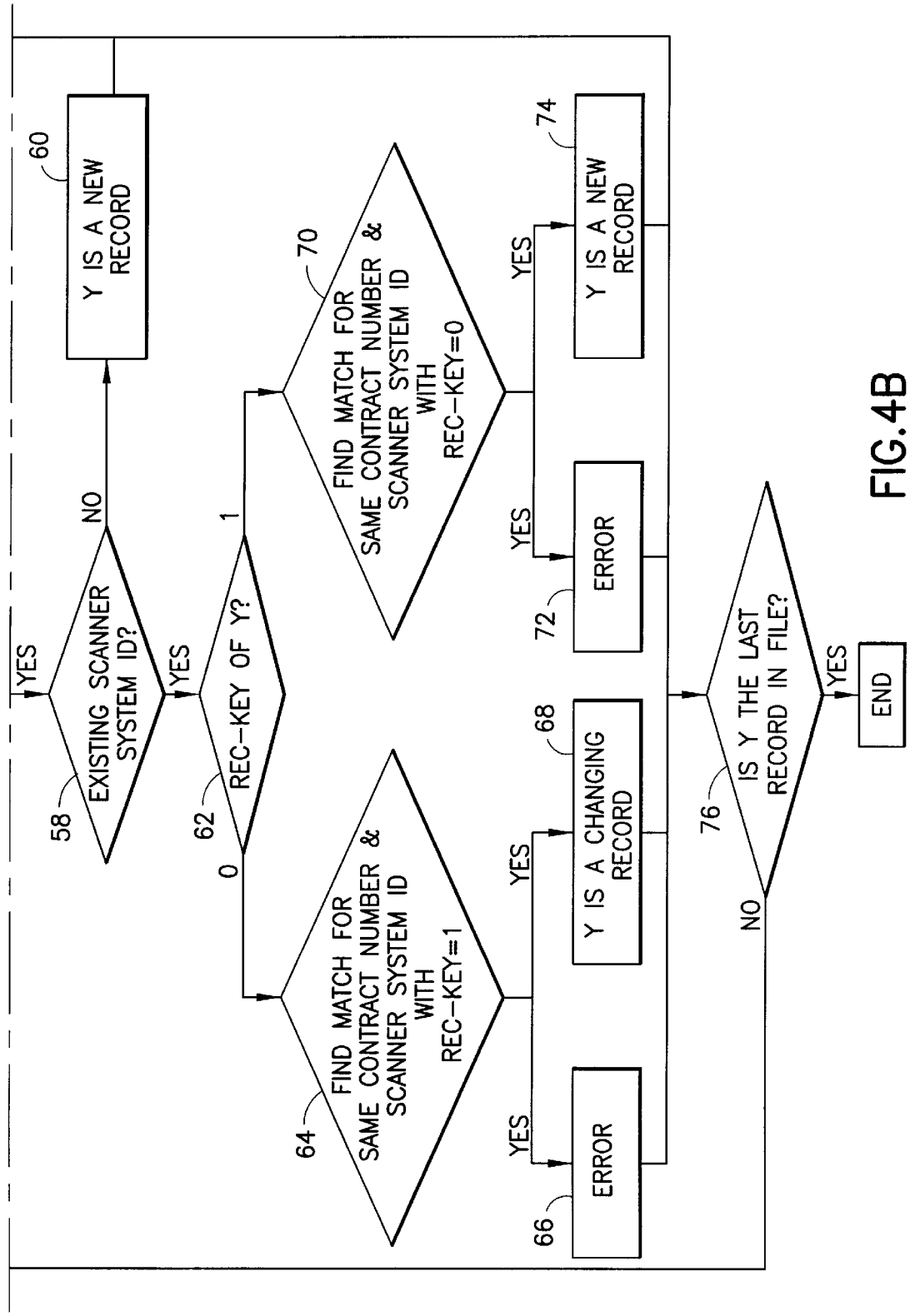

In accordance with the flowchart shown in FIG. 4, the next record Y in the Extraction Output File corresponding to an alive contract is read (step 40) by the operation server and compared to records in the current Contract Table. In accordance with the preferred embodiment of the invention, a contract from the MSA Extraction Output File that satisfies one of the following conditions is a New Record (steps 56, 60 and 74 in FIG. 4) in the Contract Table. (1) It has a Contract Number that does not previously exist in the Contract Table (as determined by decision block 54 in FIG. 4). (2) It has a System ID that does not previously exist in the Contract Table (as determined by decision block 58 in FIG. 4). (3) It has value 1 (future) for the Contract Rec-Key field, and a unique record from the Contract Table can be found with the same Contract Number and System ID (as determined by decision block 70 in FIG. 4), but value 0 (current) for the Contract Rec-Key field instead (as determined by decision block 62). A contract from the MSA Extraction Output File that satisfies the following condition is a No-Change Record (step 46 in FIG. 4) in the Contract Table: It has a full match of all data fields with an existing record in the Contract Table (as determined by decision block 42 in FIG. 4). A contract from the MSA Extraction Output File that satisfies one of the following conditions is a Changing Record (steps 52 and 68 in FIG. 4) in the Contract Table: (1) A unique record can be found from the Contract Table of its same Contract Number, System ID and Contract Rec-Key, but it has different values for at least one other field with that record (as determined by decision block 48 in FIG. 4). (2) A unique record can be found from the Contract Table of its same Contract Number and System ID, but the Contract Rec-Key value 1 (as determined by decision block 64 in FIG. 4), while it has value 0 (as determined by decision block 62). This represents a matured future contract. A record in the Contract Table that is not included in the latest MSA Extraction Output File is a Removing Record. At various stages in the parsing algorithm (i.e., blocks 44, 50, 66 and 72 in FIG. 4), an Error indicator is generated if an error is detected in the data in the record being parsed.

A new record is added into the Contract Table when a New Record from the latest MSA Extraction Output File is identified. The Processing Date value is set to the current system date. The Contract Grace Period End Date value is set to a predetermined number of days after the contract end date. The Contract Status field is set to the value L (Alive). The Record Status field is set to the value A (Add). The values of all other fields are set according to the record from the MSA Extraction Output File.

The record in the Contract Table is changed as follows when it is defined as a No-Change Record. The value of the Record Status field is set to N (No Change). The values of all other fields are not changed.

The record in the Contract Table is changed as follows when it is defined as a Changing Record. The Processing Date value is not changed. The Contract Grace Period End Date value is set to a predetermined number of days after the contract end date. The value in the Contract Status field is not changed. The value in the Record Status field is set to C (Change). The values in all other fields are changed according to the record in the MSA Extraction Output File. The Changing Record, with its old and new values of all fields, is logged in an Event Log by the operation server with system time and date of the change.

A record in the Contract Table is changed as follows when it is identified as a Removing Record. The value of the Contract Status field is set to D (Dead). The value of the Record Status field is set to R (Remove) after the Contract Update File (see later) is generated based on the updated Contract Table. The values of all other fields are not changed.

The process described above generates a Contract Table by "parsing" the MSA Extraction Output File. As used herein, the term "parsing" means selecting fields in one file to determine values and then compare those values with existing field values in another file. Preferably the MSA extraction file is parsed daily after receipt by the operation server. The Record Status field of every record in the Contract Table is set to I (Initial) before parsing the MSA Extraction Output File. The operation server parses the MSA extraction file record by record using the algorithm shown in FIG. 4. Every record in the Contract Table that still has a value I in the Record Status field after parsing the MSA Extraction Output File is a Removing Record. The extraction algorithm ends when it is determined (decision block 76 in FIG. 4) that the last record in the MSA Extraction Output File has been parsed.

In accordance with a further feature of the preferred embodiment, the operation server 22 (see FIG. 2) generates a Contract Update File for the production server 28 to update its service contract information. The Contract Update File is generated daily after the parsing of the MSA Extraction Output File and the operations on the Contract Table records are completed. The Contract Update File is stored on the operation server 22, which is accessible by the production server 28. The Contract Update File consists of all Alive (contract_status is "L"), Add, Changing or Removing (record_status is "A", "C" or "R", respectively) Records from the Contract Table. No Change Records (record_status is "N") are not copied to the Contract Update File. The Contract Update File is preferably in XML format. The data fields for the records will be copied from the Contract Table.

A database table, named Log Receipt History Table, is also created and maintained to track the history of log data received from scanners. Every log file received by the operation server will have one and only one record in the Log Receipt History Table. Every scanner may have multiple records in the table representing multiple log files from the same scanner. Every record in the Log Receipt History Table will have the following data fields. (1) The primary key is the ID field, which is a number sequence auto-generated when the record is inserted. (2) A System ID field holding the System ID of the scanner that sends the log file. (3) A Received Date Time file having the date and time when the log file was received by the data preprocessor. (4) A File Size field containing the size of the log file received. (5) A Days Since Last Receipt file holding the number of days between the last file received and this file receipt date.

A new record is added into the Log Receipt History Table by the data preprocessor when a new log file is received and processed. A record in the Log Receipt History Table will not be changed or removed once it is added.

In accordance with the preferred embodiments of the present invention, the operation server (22 in FIG. 2) performs a periodic task which examines the data in the Log Receipt History Table and determines if the date of receipt or the volume of the most recently received data file from a particular scanner indicates that recent data collection from that scanner has been unsuccessful or incomplete.

Referring again to FIG. 2, in the event of unsuccessful or incomplete transmission by a scanner of its operational data, the operation server 22 sends a request to the automated support center 16 to reinitialize the data logging and proactive diagnostic data transfer features on that particular scanner 2. In addition, the Administration Tool incorporated in the operation server 22 keeps a record of the date, time and System ID of the scanner for each request sent to the automated support center 16 to reinitialize a scanner. The Administration Tool also causes the appropriate system administrator to be notified of the discrepancy in the data transfer from the identified scanner.

Figure 5:
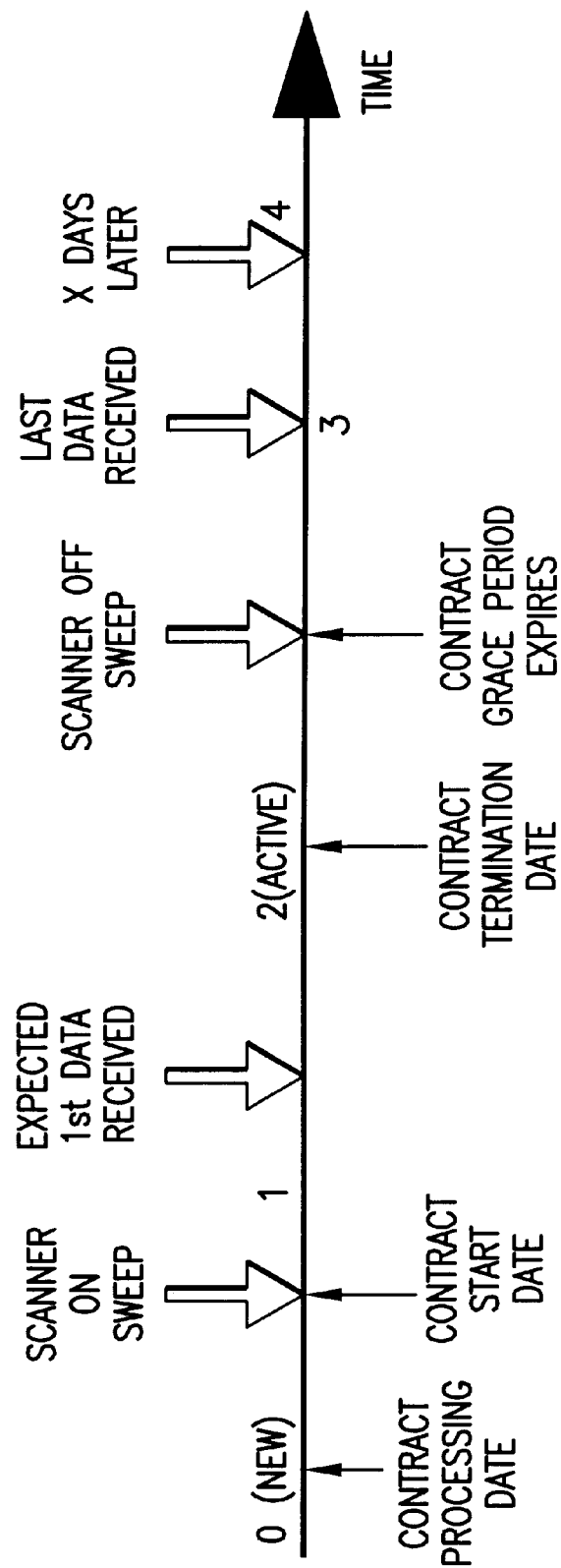
FIG. 5 is a timeline showing the life cycle for the data logging program for remote scanners in accordance with the preferred embodiments of the invention.

In accordance with the preferred embodiment, the operation server also maintains a database table, named Scanner Status Table, to track the data logging service status of each scanner that has a valid contract(s). Any future contract is not included in the Scanner Status Table until it becomes current. Every scanner that is covered by a valid scanner utilization reporting service contract will have one and only one non-terminated record in the Scanner Status Table. FIG. 5 shows the life cycle of the data logging program on a scanner.

Referring to FIG. 5, every scanner that has utilization reporting service has the following threshold dates in its service life cycle. The Scanner On Sweep date is the scheduled date that the automated support center (16 in FIG. 2) will perform a sweep that turns on the data logging feature on a scanner. The Scanner On date should be the same as the start date in the contract covering that scanner. The Expected First Data Received date is the expected date that the operation server (22 in FIG. 2) will receive the first log data transmission from the scanner. The Last Data Received date is the actual last date that the operation server receives log data from the scanner. The Scanner Off Sweep date is the scheduled date that the automated support center performs a sweep to turn off the data logging feature on the scanner. The Scanner Off date should be the same as the expiration date of the grace period following contract termination. No log file will be received from the scanner once the automated support center "scanner off" sweep is successful.

Every scanner that is covered by a utilization reporting service contract will have following status in its service life cycle: 0 (New) the scanner has.no active service; 1 (Being Turned On) service on the scanner is being turned on; 2 (Active) the scanner has active service; 3 (Being Turned Off) service on the scanner is being turned off; 4 (Terminated) service on the scanner is already terminated.

In addition, as seen in Table 2 (see Appendix), the following data fields are defined in the Contract Table and used for scanner status threshold date calculations. For each current contract in the Contract Table, the Processing Date field holds the date that the operation server first processed the contract. The Contract Table also includes a Contract Grace Period End Date field. The service may not be terminated immediately after the contract end date. The service may remain active for a predetermined grace period. For each current contract in the Contract Table, the Grace Period End Date field is set as a predetermined configurable time period after the contract end date.

The scanner status threshold dates are calculated as follows. The Scheduled Sweep On date, for a contract, is the later of the Processing Date and the Contract Start Date in the Contract Table; and for a scanner, is the earliest scheduled "scanner on" sweep date for all its current contracts. The Expected 1st Data Received date is initially scheduled and later updated when the first data is actually received. The Last Data Received date is set as the latest log receiving date for the scanner according to the Log Receipt History Table. The Scheduled Sweep Off date, for a contract, is the Grace Period End Date; and for a scanner, is set as the latest grace period end date for all its current contracts. Every record in the Scanner Status Table has data fields as defined in Table 3 (see Appendix). The primary key is the System ID field.

The operation server also maintains a database table, named Scanner Status Audit Table, to keep track of all the inserts/changes to the Scanner Status Table. The scanner status audit table preferably has fields for the :old and :new values of all fields of Table 3 except field No. 5 (Last Received Date). It also has a field for the Time/Date stamp when the audit record is inserted. To track inserts, an Insert Trigger is placed on the Scanner Status Table so that the inserted record can be added to the :new value fields of the Scanner Status Audit Table. To track changes, Change Triggers are placed on the Scanner Status Table so that changed records can be added to the Scanner Status Audit Table with the :old and :new values. The Scanner Status Table will fire the Change Trigger when any field marked as "Yes" in the "Change Audit?" column of Table 3 is changed.

Figure 6:
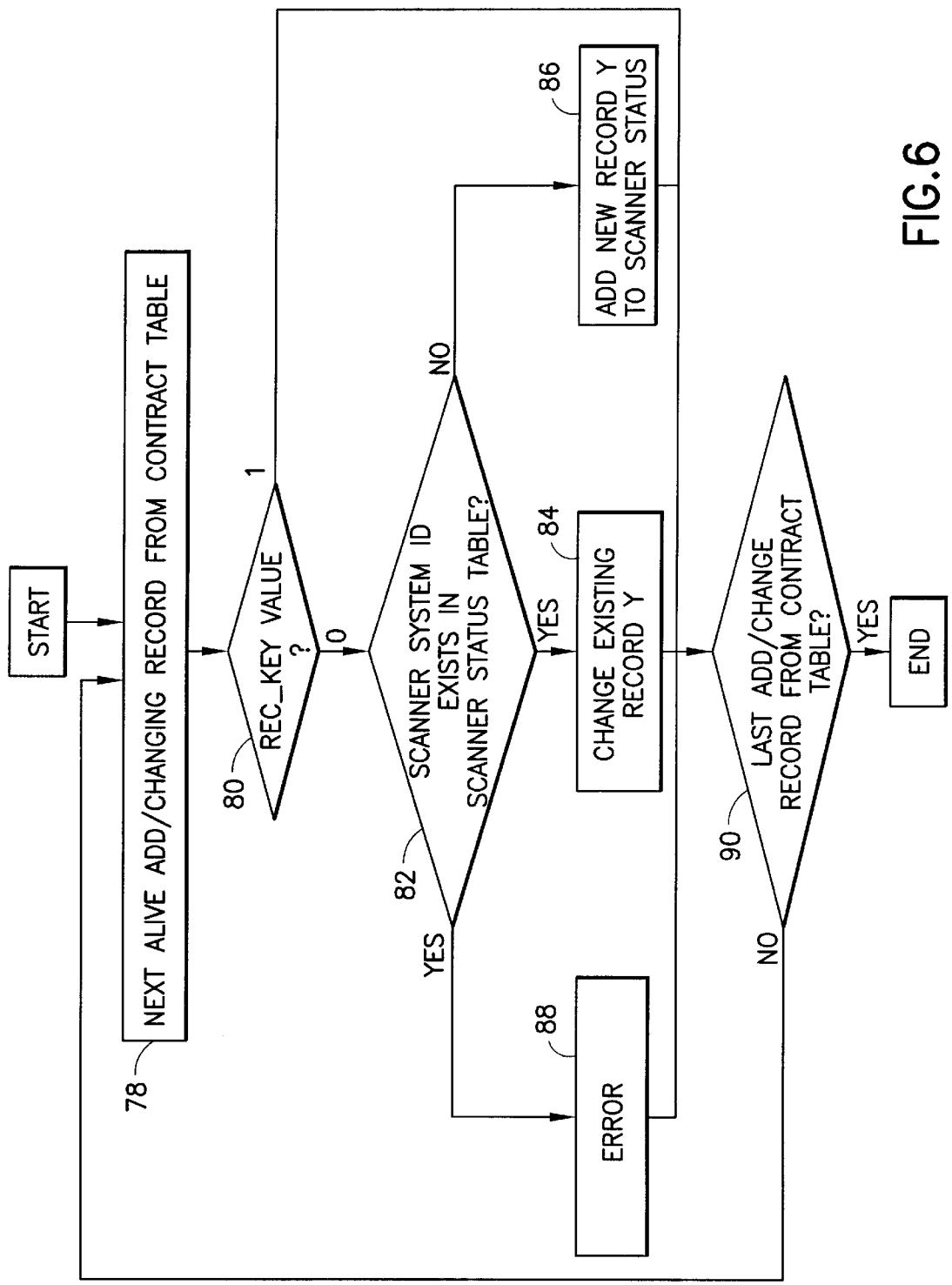
FIG. 6 is a flowchart showing the steps of a method for generating a Scanner Status Table from Add/Change Records of a Contract Table in accordance with the preferred embodiments of the invention.

The Scanner Status Table is preferably updated daily after the Contract Table is updated. The operation server generates the Scanner Status Table by parsing all Add and Changing Records from the Contract Table, as shown in FIG. 6. The algorithm retrieves the next Alive Add/Changing Record from the Contract Table (step 78). In step 80, the algorithm determines whether the value in the Contract Rec-Key field for the retrieved record is 0 (indicating a current contract) or 1 (indicating a future contract). If the value equals 0, the algorithm determines whether the System ID for the record being processed exists in the Scanner Status Table (step 82). The Scanner Status Table record operations include adding a new record (step 86 in FIG. 6) if the System ID does not exist in the Scanner Status Table and changing an existing record (step 84 in FIG. 6) if the System ID exists in the Scanner Status Table and there is no error. An Error indicator is generated (step 88) if an error is detected in the data in the record being parsed. The algorithm ends when it is determined (decision block 90 in FIG. 6) that the last Add/Changing record from the Contract Table File has been parsed. The algorithm proceeds directly from step 80 to step 90 if the Contract Rec-Key value equaled 1.

In accordance with the preferred embodiment, a new record is added into the Scanner Status Table based on the following: (1) The System ID value is be set according to the System ID of the record from the Contract Table. (2) The Sweep On Date field is set to the later of the Processing Date and the Contract Start Date of the record from the Contract Table. (3) The Sweep On Attempts field is set to the number of sweep attempts to turn service on (default to 0). (4) The First Received Date field is set according to the proactive diagnostic schedule generated by the automated support center (16 in FIG. 2). (5) The value of the Last Received Date field is set to Null. (6) The Sweep Off Date field is set to the Contract Grace Period End Date of the record from the Contract Table. (7) The Sweep Off Attempts field is set to 0. (8) The value of the Status field is set to 4 (Terminated) if the Room Status field of the record in the Contract Table has the value 9X. The value will be set to 0 (New) otherwise.

An existing record in the Scanner Status Table is modified as follows: (1) The System ID value is not changed. (2) If the Current Status field has value 0 (New), then the Sweep On Date value will be changed to the sooner of the current value and the contract scheduled sweep on date derived from the record from Contract Table. If the Current Status field has a value other than 0 (New), then the value is not be changed. (3) The value in the Sweep On Attempts field is not changed. (4) The First Received Date field is changed according to the proactive diagnostic schedule generated by the automated support center. (5) The value in the Last Received Date field is not changed. (6) The value in the Sweep Off Date field is changed to the later of the current value and the Contract Grace Period End Date of the record from the Contract Table. (7) The Sweep Off Attempts field is not changed. (8) The value of the Status field is set to 4 (Terminated) if the Room Status field of the record in the Contract Table has the value 9X. The value will not be changed otherwise.

Figures 7, 7A:
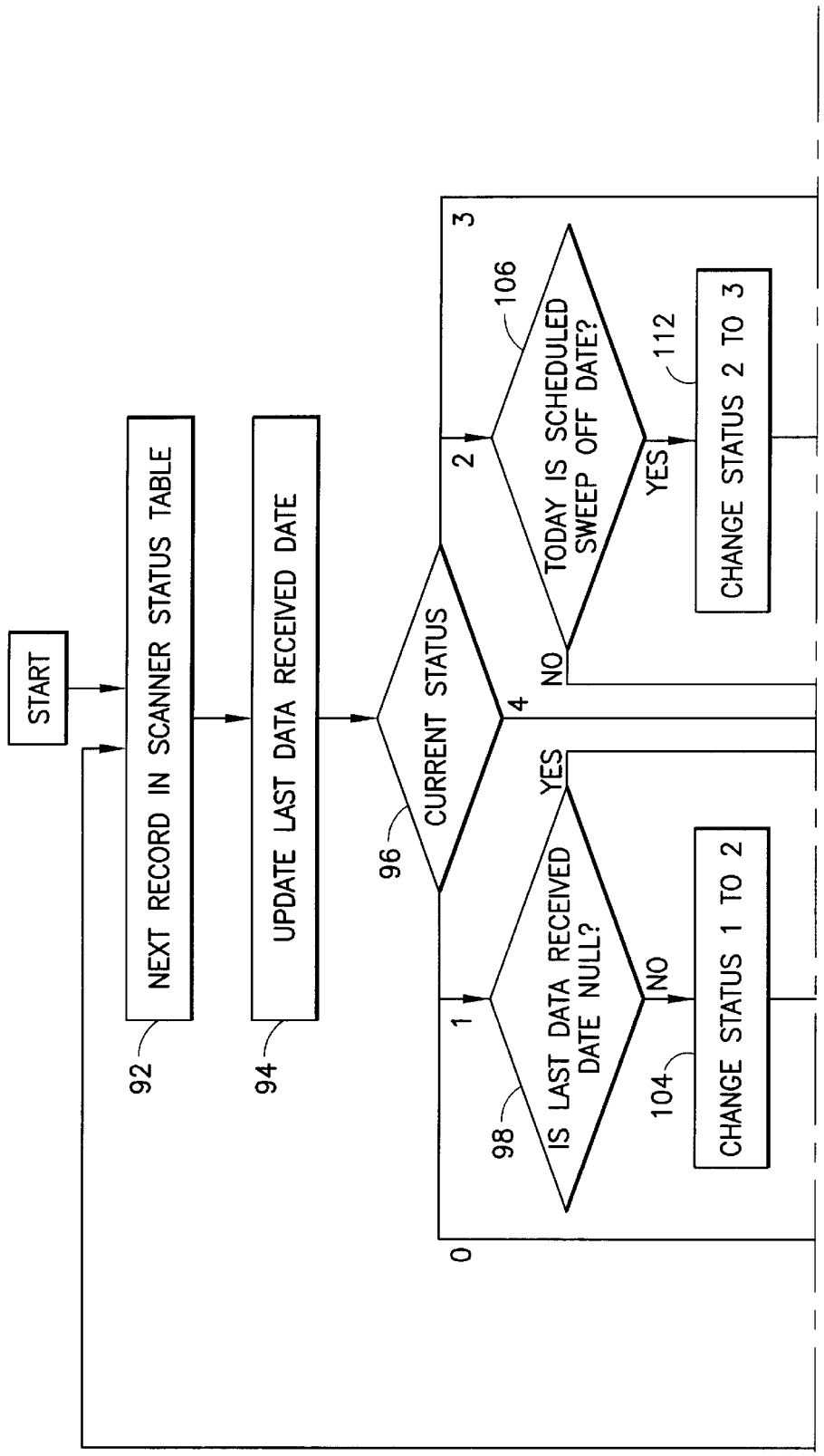
FIG. 7 is a flowchart showing the steps of a method for updating the status of scanners recorded in a Scanner Status Table in accordance with the preferred embodiments of the invention.
Figure 7B:
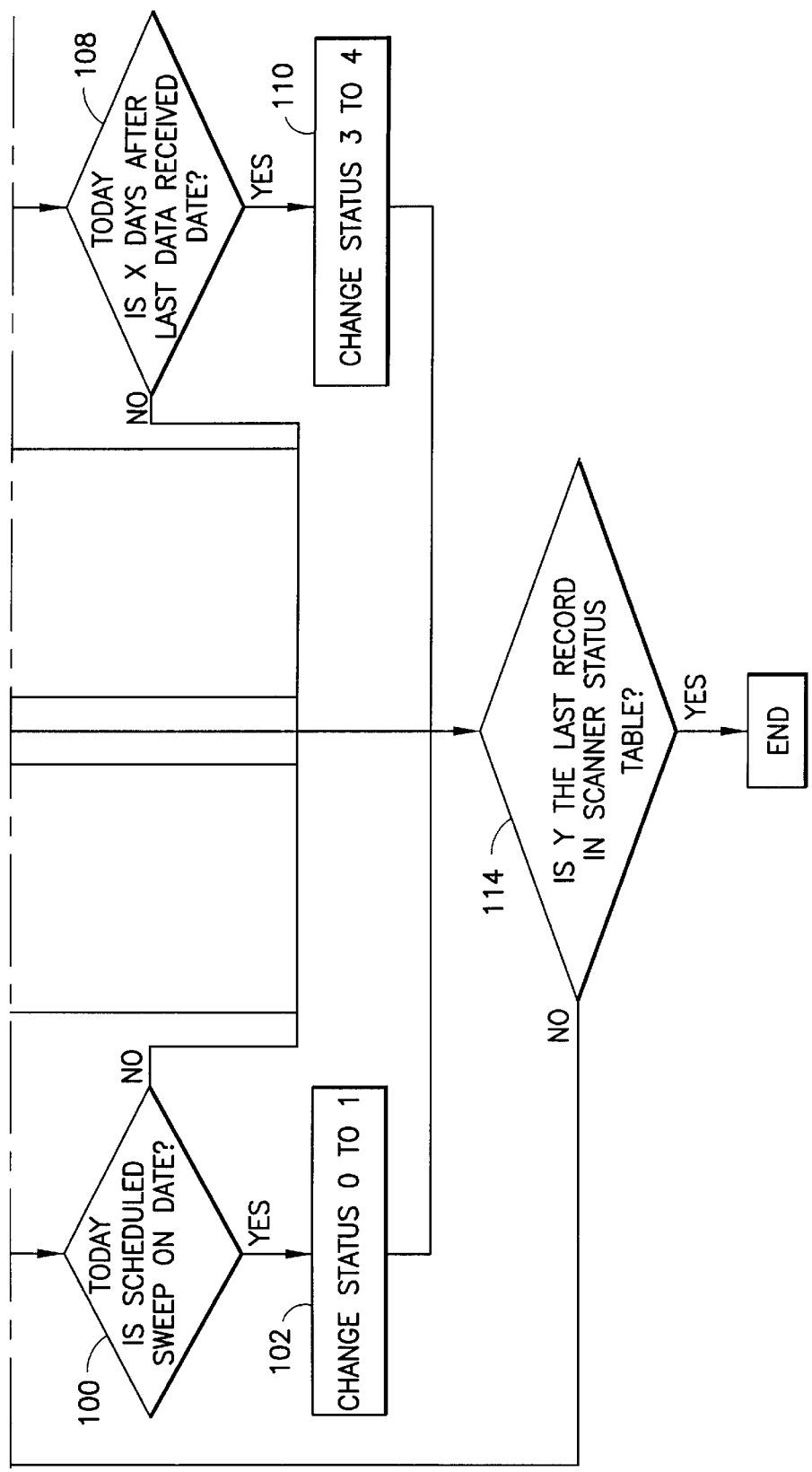

In accordance with the preferred embodiment of the invention, the status of all scanners is updated daily after the Scanner Status Table is updated based on the Contract Table. The operation server updates the status of all scanner records in the Scanner Status Table using the algorithm shown in FIG. 7. The algorithm retrieves the next record in the Scanner Status Table (step 92). In step 94, the Last Received Date field is updated based on the Log Receipt History Table. In step 96, the algorithm determines the current value in the Status field of the record being processed.

If the Status field has the value 0 (New), the algorithm determines whether that day is scheduled as the Scanner On Sweep date (step 100). If "Yes", then the scanner status is changed from 0 to 1 (step 102) and the value in the Sweep On Attempts field is incremented by 1. The value of all other fields is not changed. The operation server (22 in FIG. 2) then sends an e-mail to the automated support center (16 in FIG. 2), requesting the latter to remotely enable the data logging feature and proactive diagnostic data transfer on the scanners. Then the algorithm determines whether the record being processed is the last record in the Scanner Status Table (step 114). If "No", then the algorithm proceeds directly to step 114. If the record just processed is the last record, the algorithm ends. If it is not the last record, the algorithm returns to step 92 and processes the next record.

If the Status field has the value 1 (Being Turned On), the algorithm determines whether the Last Received Date is Null (step 98) today is scheduled as the Scanner On Sweep date (step 100). If "Yes", then the algorithm proceeds to step 114. If "No", then the scanner status is changed from 1 to 2 (step 104), before proceeding to step 114.

If the Status field has the value 2 (Active), the algorithm determines whether that day is scheduled as the Scanner Off Sweep date (step 106). If "Yes", then the scanner status is changed from 2 to 3 (step 112) and the value in the Sweep Of f Attempts field is incremented by 1. The value of all other fields is not changed. The operation server (22 in FIG. 2) then sends an e-mail to the automated support center (16 in FIG. 2), requesting the latter to remotely disable the data logging feature and proactive diagnostic data transfer on the scanners. Then the algorithm proceeds to step 114. If "No", then the algorithm proceeds directly to step 114.

If the Status field has the value 3 (Being Turned Off), the algorithm determines whether that day is X days after the Last Received Date (step 108). If "Yes", then the algorithm proceeds to step 114. The value of X is configurable. If "Yes", then the scanner status is changed from 3 to 4 (step 110), before proceeding to step 114. If "No", then the algorithm proceeds directly to step 114.

The data preprocessor (incorporated in operation server 22 shown in FIG. 2) performs the initial processing of scanner data after it has been sent to the automated support center. This initial processing (shown in FIG. 8) consists of periodically checking for and collecting new scanner files (step 116), identifying the type of scanner the file came from, verifying the fields in the scanner file (step 118), generating the CPT codes (step 120), converting the scanner file to an XML format (step 122) and transferring the file to the production server. A history of the data preprocessor activities, that includes which scanner files were processed, when they were processed, how long the processing took, and any errors associated with the processing, is available to the system administrator in a web-delivered format. If any scanners are not sending the files as they should or processing errors are encountered, the data preprocessor will notify the system administrator.

Figure 8:
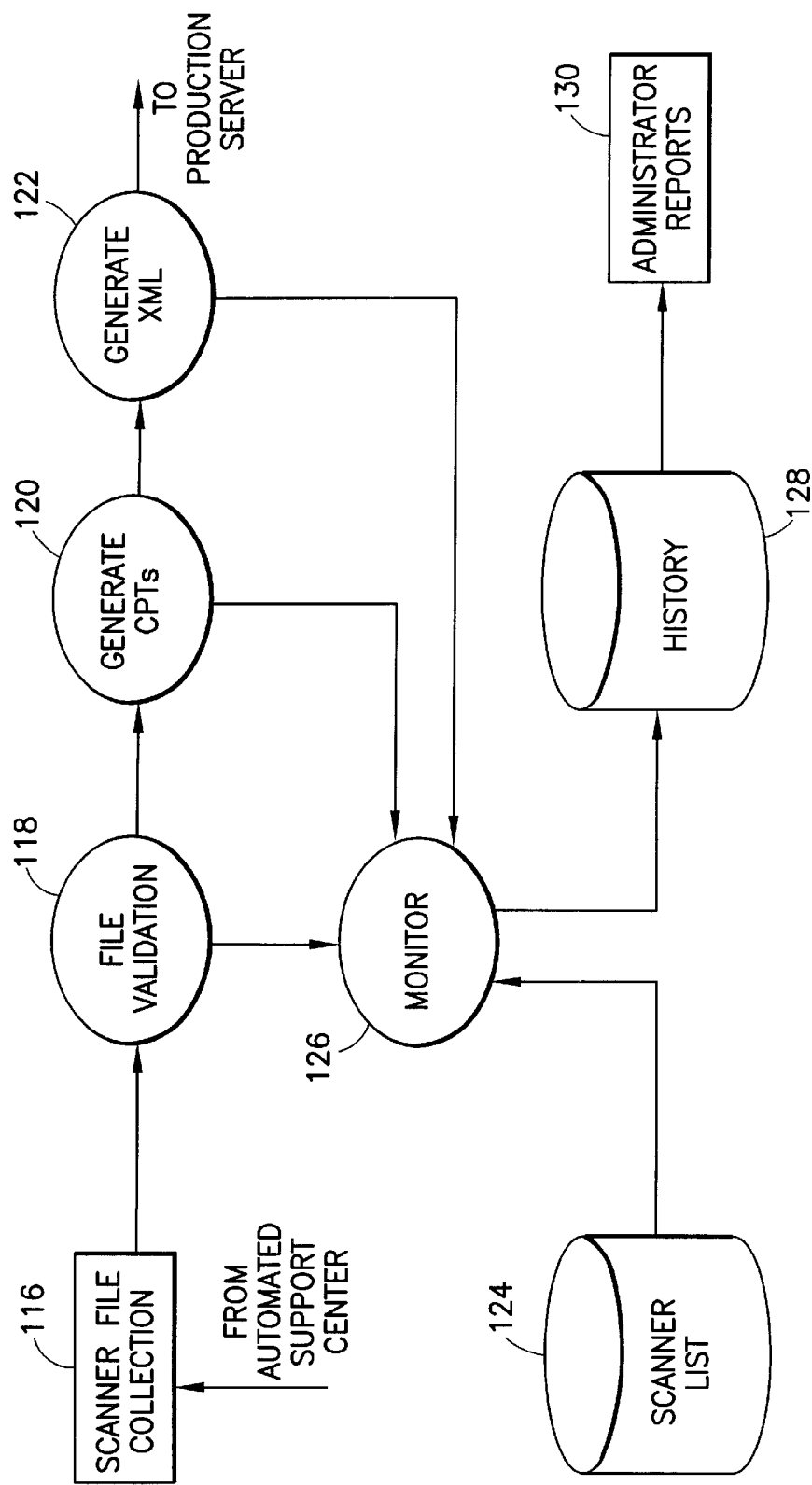
FIG. 8 is a diagram showing the flow and processing of scanner operational data in a data preprocessor in accordance with the preferred embodiments of the present invention.

The data preprocessor automatically detects when, new scanner files have arrived from the automated support center and then validate these files (step 118 in FIG. 8). Some files may need to be uncompressed. The data preprocessor identifies the file "grammar" (e.g., MR or CT) and will log any unknown grammar as an error. The data preprocessor also verifies that all fields needed to provide the service at issue are present in the record, of the correct type and in the correct range. The data preprocessor tries to preserve as much of the raw scanner file as possible. If the record is not complete (i.e., has a missing field), the record will be logged and deleted. If the record deleted is at a level that encompasses other records, then the records it encompasses will also be deleted (e.g., a deleted exam record will cause all subsequent records until the next exam record to be deleted). If the exam or series number in a record is replicated, then subsequent records are renumbered to correct this. The data preprocessor also generates CPT codes based on a reference document.

The data preprocessor monitors (step 126) and records (step 128) its activities and reports those activities to the system administrator (step 130). In particular, the data preprocessor records the time and day that a scanner file is received from the automated support center and the size of the file (in the Log Receipt History Table); the start and end time and day that a scanner file is processed (this should be accessible via the system ID; and any errors associated with the processing of a scanner file (again this should be accessible via the system ID). In addition, the data preprocessor will periodically check all scanners that are enabled for data logging and report generation (step 124), and verify that these scanners have been sending data. The rate at which this check is done is configurable. The data preprocessor will notify the system administrator of any error conditions or inactive scanners. Also the data preprocessor logs the number of files transferred to the production server. The data preprocessor sends processed XML files to the production server (28 in FIG. 2) after compressing them as soon as processing is complete. The data preprocessor sends a Transfer Log file to the production server (28 in FIG. 2) once per day. The data preprocessor delivers dynamic HTML reports that show the number of files processed, processing time statistics and error logs, i.e., files processed per day, week, month, and year, and average, minimum and maximum time to process a file; scanner file statistics on all system ID's as well as on an individual system ID, i.e., time received per system ID and all system ID's; and file size per system ID and all system ID's; and the expected date that a system ID should deliver data along with a status.

In accordance with a further aspect of the invention, the operation server is programmed with a web-based administration tool functionality, which includes event logging and reporting. The Administration Tool maintains a "Log File" (not necessarily in a file structure) to keep a record of the following activities: date and time when MSA Extraction Output File fetching failed; date, time and file size of the MSA Extraction Output File received; date, time and total number of MSA Extraction Output File records parsed; date, time, and error conditions in the extraction algorithm and related contract table; date, time, and number of New Records, number of No Change Records, number of Changing Records, and number of Removing Records in the Contract Table; date, time, file size, number of New Records, number of Changing Records, and number of Removing Records in the Contract Update File; date, time, and file size for the Contract Update File sent to/retrieved by the production server; date and time when New Record added in Scanner Status Table; date, time, and old and new values of Changed Records in the Scanner Status Table; and date, time, sweep type and System ID of the e-mail requests sent to the automated support center to turn on/off a scanner.

In addition, the Administration Tool provides different reports on request. For example, the New Customer Tracker report includes all scanners that are covered by new utilization reporting service contract(s) and are not yet in the production mode. From the Scanner Status Table, all scanners with status 0 (New) and 1 (Being Turned On) are included in this list. For each listed scanner, the report will have the following information: Customer Name, Scanner System ID, Contract Start Date(s), Service Turn On Date, Number of Sweep On Attempts, Expected First Data Receipt Date, Status and Assistance. For all scanners listed in this report, the Scanner System ID, Service Turn On Date, Number of Sweep On Attempts, and Expected First Data Receipt Date information are retrieved from the System ID, Sweep On Date, Sweep On Attempt and First Received Date fields respectively of the Scanner Status Table.

For all scanners listed in the New Customer Tracker report, the Customer Name and Contract Start Date(s) information is retrieved from Customer Name and Contract Start Date fields in the Contract Table respectively. For a scanner covered by multiple scanner utilization reporting service contracts in the Contract Table, all Contract Start Dates are retrieved and listed.

Each scanner listed in the New Customer Tracker Report will have one of the following status: (a) a scanner has a Green status if the system date is before the Expected First Data Receipt Date; (b) a scanner has a Yellow status if the system date is within 2 days after the Expected First Data Receipt Date; (c) a scanner has a Red status if the system date is at least 2 days after the Expected First Data Receipt Date.

Assistance is available only when the Status is Red and the scanner's Current Status is 1 (On) from Scanner Status Table. When an assistance request is issued by the operation server, an e-mail is sent to the automated support center, requesting remote enabling of the data logging feature and the proactive diagnostic data transfer on this scanner. In the Scanner Status Table, this scanner's Sweep On Date field is reset to the system date. The Expected First Data Receipt Date field in the New Customer Tracker report is reset to a predetermined configurable period after the scheduled Service Turn-On Date. The Number of Sweep On Attempts is incremented by 1. Manual Intervention is expected when the Number of Sweep On Attempts is greater than 2. The New Customer Tracker report is generated in real-time through database queries when it is requested.

The Administration Tool can also generate an Expiring Customer Tracker report. This tracker includes all scanners that are covered by expiring utilization reporting service contracts. This list includes all scanners from the Scanner Status Table having a status 3 (Off) or status 2 (Active) but in the contract grace period. For each listed scanner, the Expiring Customer Tracker report will have the following information: Customer Name, Scanner System ID, Contract End Date(s), Service Turn Off Date, Number of Sweep Off Attempts, Last Data Receipt Date, Status and Assistance. For all scanners listed in this report, the Scanner System ID, Service Turn Of f Date, Number of Sweep Off Attempts, and Last Data Receipt Date information are retrieved from the System ID, Sweep Off Date, Sweep Of f Attempts and Last Received Date fields respectively in the Scanner Status Table. For all scanners listed in this report, the Customer Name and Contract End Date(s) information is retrieved from the Customer Name and Contract End Date fields respectively of the Contract Table. For a scanner having multiple service contracts in the Contract Table, all Contract End Dates are retrieved and listed.

Each scanner listed in the Expiring Customer Tracker report will have one of the following status: (a) a scanner has a Green status if the Last Data Receipt Date is before the Service Turn Off Date; (b) a scanner has a Yellow status if the Last Data Receipt Date is within 1 week after the Service Turn Off Date; and (c) a scanner has a Red status if the Last Data Receipt Date is beyond 1 week after the Service Turn Off Date.

Assistance is available only when the Status is Red and the scanner's Current Status is 3 (Off) from the Scanner Status Table. When a request for assistance is issued, an e-mail is sent by the operation server to the automated support center, requesting remote disabling of the data logging feature and the proactive diagnostics data transfer on this scanner. In the Scanner Status Table, this scanner's Sweep Off Date field is reset to the system date. The Sweep Off Attempt field is incremented by 1. Manual intervention is expected when the Number of Sweep Off Attempts is greater than 2. Again this report is generated in real-time through database queries when it is requested.

The Administration Tool can also generate an Active Customer Tracker report. This tracker includes all scanners that have data logging in the production mode. This list includes all scanners from the Scanner Status Table having a status 2 (Active). For each listed scanner, the Active Customer Tracker report will have the following information: Customer Name, Scanner System ID, Turned On Date, Last Data Receipt Date, Next Data Expected Date, Last Received File Size and Status. For every scanner listed in this report, the Scanner System ID, Last Data Receipt Date and Last Received File Size information are retrieved/derived from the System ID field, the latest Received Date Time, and the File Size of the latest reception contained in the Log Receipt History Table. The Next Data Expected Date is set according to the proactive diagnostics schedule of the automated support center. For every scanner listed in this report, the Turned On Date information is retrieved from the Sweep On Date field in the Scanner Status Table and the Customer Name information is retrieved from the Customer Name field of the Contract Table.

Each scanner listed in the Active Customer Tracker report will have one of the following status: (a) a scanner has a Green status if the system date is before the Next Data Expected Date, and the Last Received File Size is larger than 15 kilobytes; (b) a scanner has a Yellow status if the system date is within 2 days after the Next Data Expected Date, or the Last Received File Size is between 5 and 15 kilobytes; and (c) a scanner has a Red status if the system date is beyond 2 days after the Next Data Expected Date, or the Last Received File Size is smaller than 5K. The Active Customer Tracker report is generated in real-time through database queries when it is requested.

The Administration Tool can also generate a Log Data History report. This tracker includes all scanners that were ever covered by a utilization reporting service contract. This list includes all scanners from the Scanner Status Table having a status 0 (New), 1 (On), 2 (Active), 3 (Off) and 4 (Terminated). For each listed scanner, the Log Data History report has the following information: Customer Name, Scanner System ID, Turned On Date, Number of Files Received, Average File Size, Average Number of Days Between Data Receipt, Current Status and Details. For every scanner listed in this report, the Scanner System ID, Number of Files Received, Average File Size and Average Number of Days Between Data Receipt information are retrieved/derived from the System ID field, number of records with this System ID, average of File Size and average of Days Since Last Receipt respectively contained in the Log Receipt History Table. For every scanner listed in this report, the Turned On Date and Current Status information are be retrieved from the Sweep On Date and Status (new, on, active, off, or terminated) fields of the Scanner Status Table, and the Customer Name information is retrieved from the Customer Name field of the Contract Table. The report is generated real-time through database queries when it is requested.

The present invention is not limited to application in automated activation and deactivation of operational data logging in medical imaging devices. The automated technique disclosed herein can be used to activate and deactivate the logging and transfer of operational data from other types of user-operated electronic devices to a central service facility.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the term "computer system" is used broadly to include a single computer, server or data processor, or a group of interconnected computers, servers or data processors. As will be readily appreciated by persons skilled in the art, two data processing functions can be implemented as separate software modules or computer programs on separate computers or servers, or as separate software modules or computer programs on the same computer or server. As used in the claims, the phrase "adding a record to a database" includes both importing a new record and changing field values in an existing record to match a new record.

Appendix

© GE Medical Technology Services, Inc., 2000.

TABLE 1

Data Definition of Extraction Output File

| No | Field Name | Comment | Type |
|---|---|---|---|
| 1 | Service Contract Location | The location code for the service contract. Service contracts may have same numbers in different locations. | Char(4) |
| 2 | Contract Number | Service contract number. | Char(7) |
| 3 | Contract Rec-Key | Possible values include: 0 for current contract; 1 for future contract. A future contract may be a renewal of an existing current contract with the same contract number. | Char(1) |
| 4 | Corporate Name | Name of the multi-hospital corporate that signs the contract. Derived from Facility ID, Service Membership Number or National Account Code. | Char(30) |
| 5 | Customer ID | Customer ID. Key to identify a hospital. | Char(6) |
| 6 | Customer Name | Name of the hospital covered under the contract. | Char(30) |
| 7 | Billing Account Number | Billing Account Number associated with the scanner System ID. Every customer (hospital) may have multiple Billing Account Numbers. | Char(11) |
| 8 | Facility ID | Used to identify hospital and corporate grouping relationship. | Char(10) |

TABLE 1-continued

Data Definition of Extraction Output File

| No | Field Name | Comment | Type |
|---|---|---|---|
| 9 | Service Membership Number | Used to identify hospital and corporate grouping relationship. | Char(7) |
| 10 | National Account Code | Used to identify the hospital and corporate grouping relationship when the corporation is a Corporate Account. | Char(4) |
| 11 | Street Address - Line 1. | Street address of the hospital. | Char(30) |
| 12 | Street Address - Line 2. | Street address of the hospital. | Char(30) |
| 13 | Street Address - Line 3. | Street address of the hospital. | Char(30) |
| 14 | City | City of the hospital. | Char(16) |
| 15 | State | State of the hospital. | Char(2) |
| 16 | Country Code | Country code of the hospital. | Char(2) |
| 17 | Postal Code | Postal code of the hospital. | Char(10) |
| 18 | System ID | Unique ID for a scanner for a particular customer at a particular location. | Char(15) |
| 19 | Contract Room # | A serial number starting from 1 up to 99 representing every scanner covered in the same contract. | Char(3) |
| 20 | USN | Unique System Number. Unique key for a scanner, regardless of time, location and ownership | Char(10) |
| 21 | MLN | Mobile Location Number. Used to track the particular location of the scanner at a particular time. Unique in conjunction with USN. Starting from 9999 going down. | Char(4) |
| 22 | Modality Code - 4 | Modality code (long) for scanner. | Char (4) |
| 23 | PSI Description | Description of scanner product line. | Char(30) |
| 24 | SPC Description | It may be a more appropriate choice for product line than PSI Description, which is a lower level product line description. Not always available. | Char(30) |
| 25 | Contract Room Start Date | The start date of the contract on the scanner (format: YYYYMMDD) | Char(8) |
| 26 | Contract End Date | The end date of the contract. Note: all scanners covered in the same contract have the same end date. (format: YYYYMMDD) | Char(8) |
| 27 | Room Status | The status of the scanner: 07 = contract expired but service not terminated; 9X = service terminated; all other values = contract active. | Char(2) |
| 28 | Date Contract Signed | It is not a mandatory field from MSA database. May be blank. (Format: YYYYMMDD) | Char(8) |
| 29 | Feature Code (SP 0) | Feature code for Tier 0. | Char(4) |
| 30 | Feature Value (SP 0) | Yes or No. | Char(10) |
| 31 | Feature Code (SP 1) | Feature code for Tier 1. | Char(4) |
| 32 | Feature Value (SP 1) | Yes or No. | Char(10) |
| 33 | Feature Code (SP 2) | Feature code for Tier 2. | Char(4) |
| 34 | Feature Value (SP 2) | Yes or No. | Char(10) |
| 35 | Feature Code (SP 3) | Feature code for Tier 3. | Char(4) |
| 36 | Feature Value (SP 3) | Yes or No. | Char(10) |
| 37 | Feature Code (SP 4) | Feature code for Tier 4. | Char(4) |
| 38 | Feature Value (SP 4) | Yes or No. | Char(10) |
| 39 | Feature Code (SP 5) | Feature code for Tier 5. | Char(4) |
| 40 | Feature Value (SP 5) | Yes or No. | Char(10) |
| 41 | User Contact - First Name | The user contact information for Web Application initial setup. | Char(30) |
| 42 | User Contact - Last Name | Same as above. | Char(30) |
| 43 | User Contact - Phone Number | Same as above. | Char(20) |
| 44 | User Contact - Email Address | Same as above. | Char(50) |

© GE Medical Technology Services, Inc. 2000.

TABLE 2

Data Definition of Operation Server Contract Table

| No | Field Name | Comment | Type | Null? | Change Audit? |
|---|---|---|---|---|---|
| 1 | Service Contract Location | Same as Table 1.1 | | Not Null | Yes |
| 2 | Contract Number | Same as Table 1.2 | | Not Null | Primary key. |
| 3 | Contract Rec-Key | Same as Table 1.3 | | Not Null | Yes |

TABLE 2-continued

Data Definition of Operation Server Contract Table

| No | Field Name | Comment | Type | Null? | Change Audit? |
|---|---|---|---|---|---|
| 4 | Corporate Name | Same as Table 1.4 | | | Yes |
| 5 | Customer ID | Same as Table 1.5 | | Not Null | Yes |
| 6 | Customer Name | Same as Table 1.6 | | Not Null | Yes |
| 7 | Billing Account Number | Same as Table 1.7 | | Not Null | Yes |
| 8 | Facility ID | Same as Table 1.8 | | | Yes |
| 9 | Service Membership Number | Same as Table 1.9 | | | Yes |
| 10 | National Account Code | Same as Table 1.10 | | | Yes |
| 11 | Street Address - Line 1 | Same as Table 1.11 | | | Yes |
| 12 | Street Address - Line 2 | Same as Table 1.12 | | | Yes |
| 13 | Street Address - Line 3 | Same as Table 1.13 | | | Yes |
| 14 | City | Same as Table 1.14 | | | Yes |
| 15 | State | Same as Table 1.15 | | | Yes |
| 16 | Country Code | Same as Table 1.16 | | | Yes |
| 17 | Postal Code | Same as Table 1.17 | | | Yes |
| 18 | System ID | Same as Table 1.18 | | Not Null | Primary Key. |
| 19 | Contract Room # | Same as Table 1.19 | | | |
| 20 | USN | Same as Table 1.20 | | Not Null | Yes |
| 21 | MLN | Same as Table 1.21 | | | Yes |
| 22 | Modality Code - 4 | Same as Table 1.22 | | | Yes |
| 23 | PSI Description | Same as Table 1.23 | | | Yes |
| 24 | SPC Description | Same as Table 1.24 | | | Yes |
| 25 | Contract Room Start Date | Converted from Table 1.25. | Date | Not Null | Yes |
| 26 | Contract End Date | Converted from Table 1.26. | Date | Not Null | Yes |
| 27 | Room Status | Same as Table 1.27. | | Not Null | Yes |
| 28 | Date Contract Signed | Converted from Table 1.28. | Date | | Yes |
| 29 | Service Tier 0 | Yes or No from Table 1.30. | | | Yes |
| 30 | Service Tier 1 | Yes or No from Table 1.32 | | | Yes |
| 31 | Service Tier 2 | Yes or No from Table 1.34 | | | Yes |
| 32 | Service Tier 3 | Yes or No from Table 1.36 | | | Yes |
| 33 | Service Tier 4 | Yes or No from Table 1.38 | | | Yes |
| 34 | Service Tier 5 | Yes or No from Table 1.40 | | | Yes |
| 35 | User Contact - First Name | Same as Table 1.41 | | | |
| 36 | User Contact - Last Name | Same as Table 1.42 | | | |
| 37 | User Contact - Phone Number | Same as Table 1.43 | | | |
| 38 | User Contact - Email Address | Same as Table 1.44 | | | |
| 39 | Processing Date | Controlling service on scanners. Set as the date that Operation Server first processes the contract. | Date | Not Null | |
| 40 | Contract Grace Period End Date | Controlling service on scanners. Set as a pre-determined configurable time period after the contract end date. The service may remain active during the grace period. | Date | Not Null | Yes |
| 41 | Contract Status | The status of a record. Possible status include: L: Alive (default value); D: Dead for records that are permanently 'removed'. | Char(1) | Not Null | Yes |
| 42 | Record Status | Used by daily processing program. Indicates the status of the record since last update. Possible values include: I: Initial (default value); A: Add, for new records; R: Remove, for records that will be permanently removed; C: Change, for existing records that will be changed; N: No Change, for existing records with no change. | Char(2) | | |

© GE Medical Technology Services, Inc., 2000.

TABLE 3

Data Definition of Scanner Status Table

| No | Field Name | Comment | Type | Null" | Change Audit? |
|---|---|---|---|---|---|
| 1 | System ID | Scanner System ID. Unique key of the table. | | Not Null | Primary Key. |
| 2 | Sweep On Date | Scheduled Sweep On Date. | Date | Not Null | Yes |

TABLE 3-continued

Data Definition of Scanner Status Table

| No | Field Name | Comment | Type | Null" | Change Audit? |
|---|---|---|---|---|---|
| 3 | Sweep On Attempts | Number of sweep attempts to turn service on. Default to 0. | Short Integer | Not Null | Yes |
| 4 | First Received Date | Expected/Actual First Data Received Date. | Date | Not Null | Yes |
| 5 | Last Received Date | Last Data Received Date. Default to Null. | Date | | |
| 6 | Sweep Off Date | Scheduled Sweep Off Date. | Date | Not Null | Yes |
| 7 | Sweep Off Attempts | Number of sweep attempts to turn service off. Default to 0. | Short Integer | Not Null | Yes |
| 8 | Status | Current Status of the scanner. Possible values include: 0: New (default value); 1: Being Turning On; 2: Active 3: Being Turning Off; 4: Terminated. Default to 0. | Short Integer | Not Null | Yes |

What is claimed is:

1. A system comprising:

a multiplicity of devices at respective remote locations, each of said devices being identifiable and capable of logging operational data when a data logging function is activated, and being unable to log operational data when said data logging function is deactivated; and a computer system at a central location in communication with said multiplicity of devices, said computer system storing an updated database comprising a record identifying a device needing a change in the state of its data logging function, said computer system being programmed to perform the step of remotely changing said data logging function in said identified device from one of said activated and deactivated states to the other of said activated and deactivated states, wherein said computer system comprises an operation server for maintaining said updated database, and an automated support center server for remotely changing the state of said data logging function in said identified device in response to a request from said operation server.

2. The system as recited in claim 1, wherein said operation server is further programmed to log the time and date of and a device identifier for each request sent to said automated support center server.

3. A system comprising:

a multiplicity of devices at respective remote locations, each of said devices being identifiable and capable of logging operational data when a data logging function is activated, and being unable to log operational data when said data logging function is deactivated; and a computer system at a central location in communication with said multiplicity of devices, said computer system storing an updated database comprising a record identifying a device needing a change in the state of its data logging function, said computer system being programmed to perform the step of remotely changing said data logging function in said identified device from one of said activated and deactivated states to the other of said activated and deactivated states, wherein said updated database comprises customer profiling and service contract information.

4. A system comprising:

a multiplicity of devices at respective remote locations, each of said devices being identifiable and capable of logging operational data when a data logging function is activated, and being unable to log operational data when said data logging function is deactivated; and a computer system at a central location in communication with said multiplicity of devices, said computer system storing an updated database comprising a record identifying a device needing a change in the state of its data logging function, said computer system being programmed to perform the step of remotely changing said data logging function in said identified device from one of said activated and deactivated states to the other of said activated and deactivated states, wherein said computer system is further programmed to perform the steps of comparing records of new and old databases to identify records in said new database which do not have a full match of all data fields in said old database, and adding said identified records to said old database to form said updated database.

5. The system as recited in claim 4, wherein said comparing step comprises the step of comparing records of said new and old databases to identify a record in said new database which has a service contract number or a device identifier which does not appear in any record of said old database, said changing step comprising deactivating said data logging function.

6. The system as recited in claim 4, wherein said comparing step comprises the step of comparing records of said new and old databases to identify a record in said new database and a record in said old database which have the same service contract number and the same device identifier, but different data in contract status fields which indicate renewal of an existing service contract, said changing step comprising activating said data logging function.

7. The system as recited in claim 4, wherein said comparing step comprises the step of comparing records of said, new and old databases to identify a record in said new database and a record in said old database which have the same service contract number and the same device identifier, but different data in contract status fields which indicate a matured future service contract, said changing step comprises activating said data logging function.

8. The system as recited in claim 4, wherein said comparing step comprises the step of comparing records of said new and old databases to identify a record in said old database which does not appear in said new database, said changing step comprising deactivating said data logging function.

9. The system as recited in claim 4, wherein said computer system is further programmed to maintain a contract audit database table of audit records, each audit record comprising fields for indicating inserted or changed values of said updated database, and a field containing a time/date stamp indicating when the audit record was inserted in said contract audit database table.

10. The system as recited in claim 4, wherein said computer system is further programmed to output a contract update file comprising records added to said updated database.

11. The system as recited in claim 4, wherein said computer system is further programmed to maintain a device status database table comprising respective records for each device covered by a valid service contract and requiring data logging functionality, each record comprising a first scheduled date for turning on said data logging function and a second scheduled date for turning off said data logging function.

12. The system as recited in claim 11, wherein said computer system is further programmed to maintain a device status audit database table of audit records, each audit record comprising fields for indicating inserted or changed values of said device status database table, and a field containing a time/date stamp indicating when the audit record was inserted in said device status audit database table.

13. The system as recited in claim 11, wherein said computer system is further programmed to update the status of all scanners identified in said device status database table on a daily basis.

14. The system as recited in claim 11, wherein said computer system is further programmed to generate reports comprising information extracted from said device status database table.

15. A system comprising:
an automated central service facility connected to a multiplicity of remotely located devices via communications channels, wherein each device is programmed to log operational data in accordance with a data logging program stored in said device when said data logging program is activated, wherein said central service facility comprises:
means for remotely activating a data logging program in a device in response to acquisition of information that said data logging program should be activated;
means for receiving log files of operational data from said device in accordance with said activated data logging program;
a new database containing updated customer profiling and service contract information sufficient to identify all devices currently covered by service contracts requiring data logging functionality;
an old database containing old customer profiling and service contract information sufficient to identify all devices previously covered by service contracts requiring a data logging functionality; and
means for comparing said new and old databases to identify a device requiring activation.

16. A system comprising:
an automated central service facility connected to a multiplicity of remotely located devices via communications channels, wherein each device is programmed to log operational data in accordance with a data logging program stored in said device when said data logging program is activated, wherein said central service facility comprises:
means for remotely deactivating a data logging program in a device in response to acquisition of information that said data logging program should be deactivated;
a new database containing updated customer profiling and service contract information sufficient to identify all devices currently covered by service contracts requiring data logging functionality;
an old database containing old customer profiling and service contract information sufficient to identify all devices previously covered by service contracts requiring data logging functionality; and
means for comparing said new and old databases to identify a device requiring deactivation.

17. A method of remotely activating automatic logging of operational data in a device, comprising the steps of:
programming a device to store operational data and periodically send log files containing stored operational data to a central location via a communications channel in accordance with a data logging function when said data logging function is activated;
determining that said data logging function should be activated;
activating said data logging function in said device from said central location via said communications channel in response to said determining step;
importing a new database containing updated customer profiling and service contract information sufficient to identify all devices currently covered by service contracts requiring data logging functionality; and
retrieving an old database containing old customer profiling and service contract information sufficient to identify all devices previously covered by service contracts requiring data logging functionality,
wherein said determining step comprises the step of comparing records of said new and old databases.

18. The method as recited in claim 17, wherein said comparing step comprises the step of identifying a record in said new database which has a service contract number or a device identifier which does not appear in any record of said old database.

19. The method as recited in claim 17, wherein said comparing step comprises the step of identifying a record in said new database and a record in said old database which have the same service contract number and the same device identifier, but different data in contract status fields which indicate renewal of an existing service contract.

20. The method as recited in claim 17, wherein said comparing step comprises the step of identifying a record in said new database and a record in said old database which have the same service contract number and the same device identifier, but different data in contract status fields which indicate a matured future service contract.

21. The method as recited in claim 17, further comprising the step of monitoring receipt of log files at said central location to ensure receipt of a log file from said activated device within a predetermined time period after activation.

22. A method of remotely deactivating automatic logging of operational data in a device, comprising the steps of:
programming a device to store operational data and periodically send log files containing stored operational data to a central location via a communications channel in accordance with a data logging function when said data logging function is activated;

determining that said data logging function should be deactivated;

deactivating said data logging function in said device from said central location via said communications channel in response to said determining step;

importing a new database containing updated customer profiling and service contract information sufficient to identify all devices currently covered by service contracts requiring data logging functionality; and retrieving an old database containing old customer profiling and service contract information sufficient to identify all devices previously covered by service contracts requiring data logging functionality, wherein said determining step comprises the step of comparing records of said new and old databases.

23. The method as recited in claim 22, wherein said comparing step comprises the step of identifying a record in said old database which does not appear in said new database.

* * * * *